(12) United States Patent
Zalevsky et al.

(10) Patent No.: US 9,239,471 B2
(45) Date of Patent: Jan. 19, 2016

(54) MULTI-FOCAL LENS

(75) Inventors: Zeev Zalevsky, Rosh HaAyin (IL); Alex Zlotnik, Ashdod (IL); Shai Ben-Yaish, Petach Tiqva (IL); Ofer Limon, Kfar-Saba (IL); Ido Raveh, Neve Yarak (IL)

(73) Assignee: Brien Holden Vision Institute, Kensington, New South Wales (AU)

( * ) Notice: Subject to any disclaimer, the term of this patent is extended or adjusted under 35 U.S.C. 154(b) by 0 days.

(21) Appl. No.: 13/578,142

(22) PCT Filed: Feb. 9, 2011

(86) PCT No.: PCT/IL2011/000140
§ 371 (c)(1),
(2), (4) Date: Oct. 23, 2012

(87) PCT Pub. No.: WO2011/099001
PCT Pub. Date: Aug. 18, 2011

(65) Prior Publication Data
US 2013/0046381 A1    Feb. 21, 2013

Related U.S. Application Data

(60) Provisional application No. 61/302,588, filed on Feb. 9, 2010.

(51) Int. Cl.
*A61F 2/16*       (2006.01)
*G02C 7/02*       (2006.01)
(Continued)

(52) U.S. Cl.
CPC . *G02C 7/022* (2013.01); *A61F 2/16* (2013.01); *A61F 2/1648* (2013.01); *G02B 5/18* (2013.01);
(Continued)

(58) Field of Classification Search
CPC ....... A61F 2/16; A61F 2/1613; A61F 2/1618; A61F 2/1648; G02C 7/06; G02C 7/04; G02C 7/042–7/045
USPC .................. 623/6.27–6.31, 6.34; 351/159.05, 351/159.15, 159.35, 159.41, 159.44, 159.48
See application file for complete search history.

(56) References Cited

U.S. PATENT DOCUMENTS 3,549,240 A    12/1970    Sawatari
4,162,122 A *   7/1979    Cohen .................... 351/159.41
(Continued)

FOREIGN PATENT DOCUMENTS

CN       101510012 A      8/2009
EP       0369561 A2       5/1990
(Continued)

OTHER PUBLICATIONS
Bradburn, S. et al, "Realizations of focus invariance in optical-digital systems with wave-front coding", Applied Optics, OSA, Optical Society of America, Dec. 10, 1997, pp. 9157-9166, vol. 36, No. 35, United States.
(Continued)

*Primary Examiner* — Paul Prebilic
(74) *Attorney, Agent, or Firm* — Jones Day

(57) ABSTRACT

An imaging lens structure and method of imaging are presented. The imaging lens structure comprising a lens region defining an effective aperture of the lens structure. The lens region comprises an arrangement of lens zones distributed within the lens region and comprising zones of at least two different optical functions differently affecting light passing therethrough. The zones of at least two different optical functions are arranged in an interlaced fashion along said lens region corresponding to a surface relief of the lens region such that adjacent lens zones of different optical functions are spaced apart from one another along an optical axis of the lens structure a distance larger than a coherence length of light at least one spectral range for which said lens structure is designed.

28 Claims, 9 Drawing Sheets

(51) Int. Cl.
*G02B 5/18* (2006.01)
*G02C 7/04* (2006.01)
*G02B 27/00* (2006.01)
*G02B 27/42* (2006.01)
*G02C 7/06* (2006.01)

(52) U.S. Cl.
CPC ............ *G02B 5/1828* (2013.01); *G02B 5/1895* (2013.01); *G02B 27/0025* (2013.01); *G02B 27/0037* (2013.01); *G02B 27/0075* (2013.01); *G02B 27/4205* (2013.01); *G02C 7/04* (2013.01); *G02C 7/049* (2013.01); *A61F 2/1613* (2013.01); *G02C 7/06* (2013.01); *G02C 2202/22* (2013.01); *Y10S 977/902* (2013.01); *Y10S 977/932* (2013.01)

(56) References Cited

U.S. PATENT DOCUMENTS

| | | | |
|---|---|---|---|
| 4,736,734 A | | 4/1988 | Matsuura et al. |
| 4,778,462 A | * | 10/1988 | Grendahl ................... 623/6.27 |
| 4,923,296 A | * | 5/1990 | Erickson ................ 351/159.41 |
| 4,955,904 A | | 9/1990 | Atebara et al. |
| 5,117,306 A | | 5/1992 | Cohen |
| 5,158,572 A | | 10/1992 | Nielsen |
| 5,172,143 A | | 12/1992 | Baude et al. |
| 5,198,844 A | * | 3/1993 | Roffman et al. ......... 351/159.48 |
| 5,225,858 A | | 7/1993 | Portney |
| 5,245,367 A | | 9/1993 | Miller et al. |
| 5,260,727 A | * | 11/1993 | Oksman et al. ......... 351/159.03 |
| 5,299,062 A | | 3/1994 | Ogata |
| 5,302,477 A | | 4/1994 | Dao et al. |
| 5,482,801 A | | 1/1996 | Smith et al. |
| 5,543,966 A | | 8/1996 | Meyers |
| 5,662,706 A | | 9/1997 | Legerton et al. |
| 5,674,282 A | | 10/1997 | Cumming |
| 5,682,223 A | * | 10/1997 | Menezes et al. ............. 623/6.28 |
| 5,715,031 A | | 2/1998 | Roffman |
| 5,748,371 A | | 5/1998 | Cathey, Jr. et al. |
| 5,757,458 A | | 5/1998 | Miller et al. |
| 5,760,871 A | * | 6/1998 | Kosoburd et al. ............. 623/6.3 |
| 5,768,031 A | | 6/1998 | Yang |
| 5,788,883 A | | 8/1998 | Srivastava et al. |
| 5,822,091 A | | 10/1998 | Baker |
| 5,864,379 A | | 1/1999 | Dunn |
| 5,895,422 A | * | 4/1999 | Hauber ..................... 623/6.31 |
| 5,905,561 A | | 5/1999 | Lee et al. |
| 5,965,330 A | | 10/1999 | Evans et al. |
| 5,980,040 A | | 11/1999 | Xu et al. |
| 6,024,447 A | | 2/2000 | Portney |
| 6,069,738 A | | 5/2000 | Cathey, Jr. |
| 6,097,856 A | | 8/2000 | Hammond, Jr. |
| 6,172,957 B1 | | 1/2001 | Ogasawara |
| 6,451,056 B1 | | 9/2002 | Cumming |
| 6,474,814 B1 | | 11/2002 | Griffin |
| 6,488,708 B2 | | 12/2002 | Sarfarazi |
| 6,527,389 B2 | | 3/2003 | Portney |
| 6,533,416 B1 | | 3/2003 | Fermigier et al. |
| 6,536,898 B1 | | 3/2003 | Cathey, Jr. |
| 6,537,317 B1 | | 3/2003 | Steinert et al. |
| 6,554,424 B1 | | 4/2003 | Miller et al. |
| 6,554,859 B1 | | 4/2003 | Lang et al. |
| 6,576,012 B2 | | 6/2003 | Lang |
| 6,661,816 B2 | | 12/2003 | Delfyett et al. |
| 6,685,315 B1 | * | 2/2004 | De Carle .................. 351/159.41 |
| 7,025,454 B2 | | 4/2006 | Cathey, Jr. |
| 7,061,693 B2 | * | 6/2006 | Zalevsky ....................... 359/738 |
| 7,101,436 B2 | | 9/2006 | Taniguchi et al. |
| 7,224,540 B2 | | 5/2007 | Olmstead et al. |
| 7,365,917 B2 | * | 4/2008 | Zalevsky ....................... 359/738 |
| 7,411,743 B2 | | 8/2008 | Sugi |
| 7,569,312 B2 | | 8/2009 | Misaka |
| 7,646,549 B2 | | 1/2010 | Zalevsky et al. |
| 7,859,769 B2 | | 12/2010 | Zalevsky |
| 8,169,716 B2 | | 5/2012 | Zalevsky et al. |
| 8,531,783 B2 | | 9/2013 | Zalevsky |
| 8,573,775 B2 | * | 11/2013 | Weeber ..................... 351/159.44 |
| 8,955,968 B2 | * | 2/2015 | Zalevsky ............. G02B 5/1895 351/159.6 |
| 2003/0142268 A1 | | 7/2003 | Miller et al. |
| 2003/0197906 A1 | | 10/2003 | Furuta et al. |
| 2004/0114102 A1 | | 6/2004 | Miller et al. |
| 2004/0114103 A1 | | 6/2004 | Miller et al. |
| 2004/0145808 A1 | | 7/2004 | Cathey et al. |
| 2004/0230299 A1 | | 11/2004 | Simpson et al. |
| 2006/0082882 A1 | | 4/2006 | Wang et al. |
| 2006/0176572 A1 | * | 8/2006 | Fiala ............................. 359/643 |
| 2007/0236769 A1 | * | 10/2007 | Zalevsky ...................... 359/238 |
| 2008/0198482 A1 | | 8/2008 | Zalevsky |
| 2009/0074239 A1 | | 3/2009 | Zalevsky |
| 2009/0088840 A1 | | 4/2009 | Simpson et al. |
| 2009/0112314 A1 | * | 4/2009 | Sarver et al. .................. 623/6.17 |
| 2009/0116096 A1 | * | 5/2009 | Zalevsky et al. ............. 359/256 |
| 2009/0147378 A1 | | 6/2009 | Zalevsky et al. |
| 2009/0187242 A1 | | 7/2009 | Weeber |
| 2009/0279189 A1 | | 11/2009 | Getman et al. |
| 2009/0303432 A1 | | 12/2009 | Suzuki et al. |
| 2010/0075114 A1 | | 3/2010 | Kurihara et al. |
| 2010/0149510 A1 | | 6/2010 | Zaczek et al. |
| 2011/0082541 A1 | | 4/2011 | Zalevsky |
| 2012/0029631 A1 | * | 2/2012 | Wanders et al. ............. 623/6.27 |
| 2013/0278891 A1 | * | 10/2013 | Zhao ........................ 351/159.44 |

FOREIGN PATENT DOCUMENTS

| | | |
|---|---|---|
| JP | 2137815 A | 5/1990 |
| WO | 9957599 A1 | 11/1999 |
| WO | 0135880 A1 | 5/2001 |
| WO | 03012528 A2 | 2/2003 |
| WO | 03032825 A1 | 4/2003 |
| WO | 03052465 A2 | 6/2003 |
| WO | 03052492 A2 | 6/2003 |
| WO | 03076984 A1 | 9/2003 |
| WO | 2004113994 A2 | 12/2004 |
| WO | 2007141788 A2 | 12/2007 |
| WO | 2009115932 A2 | 9/2009 |
| WO | 2009140080 A2 | 11/2009 |
| WO | 2010009254 A1 | 1/2010 |

OTHER PUBLICATIONS

L. A. Carvalho, "A simple mathematical model for simulation of the human optical system based on in vivo corneal data," Revista Brasileira de Engenharia Biomedica, 2003, 19, pp. 29-37, Brazil, (Apr. 2003).

Fitzgerrell, A R et al: "Defocus transfer function for circularly symmetric pupils", Applied Optics Opt. Soc. America, Aug. 10, 1997, pp. 5796-5804, vol. 36, No. 23, United States.

Varamit, C et al: "Imaging properties of defocused partitioned pupils" Journal of the Optical Society of America (Optics and Image Science), Jun. 1985, pp. 799-802, vol. 2, No. 6, United States.

H. Wang and F. Gan, "High focal depth with pure-phase apodizer", Applied Optics, Nov. 1, 2001, pp. 5658-5662, vol. 40, No. 31, United States.

Kohn, A. . Visual adaptation: physiology, mechanisms, and functional benefits. Journal of Neurophysiol, 2007, 97 (5), pp. 3155-3164, United States, (Mar. 2007).

Webster, M.A., Georgeson, M.A., & Webster, S.M. "Neural adjustments to image blur". Nat Neurosci, 2002, 5 (9), pp. 839-840, United States—abstract only, (Sep. 2002).

Pesudovs, K., & Brennan, N.A., Decreased uncorrected vision after a period of distance fixation with spectacle wear, Optom Vis Sci, 1993, pp. 528-531, 70 (7), United States.—abstract only, (Jul. 1993).

Forrest, E.B., Eye Scan Therapy for Astigmatism, Journal of the American Optometric Association, 1984, pp. 894-901, 55(12)—abstract only, (Dec. 1984).

T. Callina and T. P. Reynolds, "Traditional methods for the treatment of presbyopia: spectacles, contact lenses, bifocal contact lenses," Ophthalmology Clinics of North America, 2006, pp. 25-33 19(1)-abstract only, (Mar. 2006).

(56) References Cited

OTHER PUBLICATIONS

C. W. Fowler and E. S. Pateras, "A gradient-index ophthalmic lens based on Wood's convex pseudo-lens," Ophthalmic and Physiological Optics,1990, pp. 262-270 10(3),—abstract only, (Jul. 1990).

Zalevsky et al, "All-optical axial super resolving imaging using a low-frequency binary-phase mask" Optics Express, OSA (Optical Society of America), Apr. 3, 2006, pp. 2631-2634, vol. 14, No. 7, Washington, DC, United States.

Sales, T R M et al, "Diffractive supperresolution elements", Journal of the optical society of America, Jul. 1997, pp. 1637-1646; vol. 14, No. 7, United States.

De Juana D M et al, "Focusing properties of annular binary phase filters", Optics Communications, Jan. 2, 2004, pp. 71-77, vol. 229, No. 1-6, North-Holland Publishing Co., Amsterdam, NL.

Webster, M., Sawides, L., Ravikumar, S., Thibos, L., Bradley, A., & Marcos, S , Adapting to astigmatism. Journal of Vision, Aug. 5, 2009, pp. 986, 986a. 9(8)—abstract only.

C. M. Sullivan and C. W. Fowler, "Progressive addition and variable focus lenses: a review," Ophthalmic and Physiological Optics, Oct. 1988, pp. 402-414 , 8(4),—abstract only.

Di Feng, Pan Ou, Li-Shuang Feng, Shu-Ling Hu, and Chun-Xi Zhang, "Binary sub-wavelength diffractive lenses with long focal depth and high transverse resolution," Opt. Express, Dec. 8, 2008, pp. 20968-20973 16, United States.

Joseph N. Mait, Axel Scherer, Oliver Dial, Dennis W. Prather, and Xiang Gao, "Diffractive lens fabricated with binary features less than 60 nm," Opt. Lett., Mar. 15, 2000, pp. 381-383, 25, United States.

Yehezkel O., Belkin M., Sagi D. & Polat U., Adaptation to astigmatic lens : effects on lateral interactions, Visual Sciences Society Annual Meeting, Sep. 23, 2005—abstract only.

Michael W. Farn, "Binary gratings with increased efficiency," Appl. Opt., Aug. 1, 1992, pp. 4453-4458, 31, United States.

Petit, R., and G. Bouchitte, "Replacement of a very fine grating by a stratified layer: homogenization techniques and the ultiplescale method," SPIE Proceedings Application and Theory of Periodic Structures, Diffraction Gratings, and Moir'e Phenomena 431, Feb. 9, 1987, vol. 815, ed. J. Lerner, France.

Yehezkel, O., Sagi, D., Sterkin, A., Belkin, M., & Polat, U., Learning to adapt: Dynamics of readaptation to geometrical distortions,Vision Research, Jul. 21, 2010, pp. 1550-1558, 50, Israel.

Hecht, E., et al., Optics, 10.2.5 The Circular Aperture, Feb. 1979, pp. 350-353, Addison-Wesley Publishing Company, Reading, Massachusetts.

Hecht, E., Optik, Dec. 1989, pp. 441-445, Addison-Wesley Publishing Company, bonn, Munchen, Germany (with partial English translation).

Webster, M., Sawides, et al., Adapting to astigmatism. D Journal of Vision, Aug. 2009, pp. 986, 986a. 9(8) (abstract only).

Sullivan, C.M., and Fowler, C.W., "Progressive addition and variable focus lenses: a review," Ophthalmic and Physiological Optics, Feb. 1988, pp. 402-14, 8( 4 ) (abstract only).

Feng, Di, et al., "Binary sub-wavelength diffractive lenses with long focal depth and high transverse resolution," Opt. Express, Dec. 2008, pp. 20968-20973, vol. 16, No. 25.

Mait, Joseph N., et al., "Diffractive lens fabricated with binary features less than 60 nm," Opt. Lett, Mar. 2000, pp. 381-383, vol. 25, No. 6.

Yehezkel, 0., et al., "Adaptation to astigmatic lens: effects on lateral interactions," Visual Sciences Society Annual Meeting, Sep. 2005 (abstract only).

Farn, Michael, "Binary gratings with increased efficiency," Appl. Opt, Aug. 1992, pp. 4453-4458, vol. 31, No. 22.

Petit, R., and Bouchitt'E, G., "Replacement of a very fine grating by a stratified layer: homogenization techniques and the multiple-scale method," SPIE Proceedings 0815, Application and Theory of Periodic Structures, Diffraction Gratings, and Moire Phenomena III, Feb. 1987, pp. 25-31, vol. 815, Ed. J. Lerner.

Yehezkel, 0., et al., "Learning to adapt: Dynamics of readaptation to geometrical distortions," Vision Research, Jul. 2010, pp. 1550-1558, 50, Israel.

Hecht, E., Optics, Chapter 10 Diffraction (Sections 10.1-10.2), May 1987, pp. 392-434, Second Edition, Addison-Wesley Publishing Company, Reading, Massachusetts.

\* cited by examiner

MULTI-FOCAL LENS

FIELD OF THE INVENTION

This invention is generally in the field of all-optical imaging techniques, and relates to an imaging multi-focal lens.

BACKGROUND OF THE INVENTION

Extending the depth of focus of imaging systems is required for various applications, including inter alia medical applications, such as endoscopic system, spectacles, and ophthalmic lenses. Various techniques have been developed to extend the depth of focus of an imaging lens.

For example, the earlier technique developed by the inventor of the present application provides for extending the depth of focus of an imaging lens unit by applying a phase coding to the effective aperture of the imaging lens unit. Various features of this technique are described for example in the following patents and published patent applications: U.S. Pat. Nos. 7,365,917; 7,061,693; US 2009/074239; US 2009/116096; U.S. Pat. No. 7,646,549, all assigned to the assignee of the present application. This technique when utilized in spectacles or ophthalmic lenses may serve as an alternative to the conventional bi- or multi-focal lens approach for patients suffering from presbyopia (i.e. different dioptric powers for distance and reading vision), where desirably extended depth of focus is achieved with the single-focus lens unit.

Various configurations of multi-focal lenses are described for example in the following patents and published patent applications:

U.S. Pat. No. 5,682,223 describes a multifocus, concentric annular ring lens wherein one of the front and back surfaces of the lens defines a central area comprising a circular disc having a spherical surface corresponding to a basic prescription Rx spherical distance optical power. A plurality of annular rings surround the central area and have alternating spherical near and distance optical powers, and at least one intermediate optical power annular ring. The immediate optical power annular ring is located in the middle or outer region of the lens optic zone, and its optical power is intermediate to the distance and near optical powers, to provide visual acuity at intermediate distances. The intermediate optical power annular ring can be placed anywhere in the middle or outer region of the lens optic zone, and can be the second annular ring from the outer edge of the lens optic zone, or can be the outermost annular ring which defines the outer circumference of the lens optic zone. The lens can be a contact lens to be worn on the cornea of the eye, such as a soft hydrogel contact lens, or can be an intraocular lens.

U.S. Pat. No. 5,158,572 describes multifocal lens having a substantially circular central region having a first optical power, surrounded by a plurality of concentric ring regions which alternate between at least two optical powers, one of which may be the first optical power. Preferably, the central region is powered for near vision. For example, one embodiment of the invention is a bifocal lens having a central near-vision portion, a first concentric ring region powered for distance vision, and a second concentric ring region having the same power as the central region.

U.S. Pat. No. 5,198,844 describes a multifocal refractive lens to focus light on the retina of the eye and method of making. The lens is comprised of a plurality of segments, alternating segments having different optical powers, at least for distance vision and another for near. The lens of the invention does not require orientation to produce adequate far and near vision and normal steroscoptic effect. One or both of the segments having the optical powers may have aspherical lens surface. Preferably, the lens has at least one aspherical lens surface and the segments are divided by an arcuate path going from the center of the lens to edge. Such a lens is manufactured by taking lens molds and cutting the molds from the edge through the center to the opposite edge along a predetermined path. The molds are cut so that the segments produced are interchangable and can be fitted together to make a mold that can produce the multifocal refractive contact lens by molding.

GENERAL DESCRIPTION

There is a need in the art for a novel approach in configuring multi-focal imaging lenses to provide extended depth of focus of the lens and allow imaging of an object from several different distances. As indicated above, imaging lenses with extended depth of focus are required in various imaging applications, including medical applications, such as spectacles and ophthalmic lenses. The term "ophthalmic lens" refers to an artificial lens for use with the eye, and includes for example intraocular lenses (IOLs), contact lenses, as well as intracorneal lenses (ICL's), corneal onlays or inlays.

The present invention provides a multi-focal lens, which defines an optical axis and has a lens region comprising two or more lens zones which are configured to apply two or more different optical functions to light passing therethrough, i.e. provide two or more different aperture codings of the light. For example, these may be zones of two or more different focal lengths and/or different phase coding (e.g. including "zero" phase coding). In the multi-focal lens of the present invention, the lens zones of different optical functions are distributed within the same region of the lens, rather than being located in spatially separated regions of the lens as, for example, in the multi-focal lenses commercially available in the market.

According to some aspects of the invention, the lens zones of different optical functions (e.g. focal lengths and possibly also phase encoding) are arranged in an interlaced pattern within the common lens region, namely said lens region is patterned with an array of lens zones where the lens zones of a first optical function are spaced from one another by one or more zones of one or more second optical functions.

In some embodiments of invention, the above-described interlaced pattern is formed as a surface relief on a surface of the lens region, such that surface parts corresponding to the lens zones of different optical functions are spaced-apart along the optical axis of the lens. Preferably, a space between the adjacent lens zones of different optical functions along said optical axis is higher than a coherence length of light at wavelength range for which the multi-focal lens has been designed (typically, light in the visible spectrum). Said space-apart arrangement of the lens zones is such that light passing through zones of different optical functions will add in intensity (squared amplitude) rather than in field (amplitude and phase), thus preventing creation of an interference pattern and desired cross terms.

The coherence length for light of a certain wavelength range is defined as the distance along which wavefronts of the light remain correlated during the light propagation. The coherence length is affected by the bandwidth (of wavelengths) of the light and by the refractive index of the media in the light propagation path. The wavefronts of two components of light (e.g. different wavelengths) propagating along the same axis/path accumulate phase with slightly different rates. For a distance shorter or equal to the coherence length, the phases of different components may be correlated, but after propagating a distance longer than the coherence length the correlation between the phases of the different components become very low. The coherence length, $\Delta Z$, of light of a certain wavelength range is defined as follows:

$$\Delta Z = \frac{c}{n\Delta v} = \frac{\lambda^2}{\Delta \lambda} \quad (1)$$

where c is the speed of light, n is the refraction index of media in which the light propagates, $\lambda$ is the central wavelength for which the element is designed, $\Delta \lambda$ is the bandwidth of wavelengths and $\Delta v$ is the spectral bandwidth of the light. Considering the use of white light illumination, the coherence length is very short (i.e. equals to several wavelengths only). Wavefronts separated by a distance larger than the coherence length are no longer correlated in phase, i.e. the temporal phase change in the two wavefronts varies in a non-correlated manner. Hence, interference of light components passing through adjacent zones of different optical functions spaced apart along the optical axis a distance larger than the coherence length is smeared, and effectively such light components add in intensity rather than in field, thus preventing formation of an interference pattern.

Preferably, the multi-focal lens of the invention is configured such that said lens region, containing multiple lens zones of different optical powers, is substantially not diffractive. In other words, a pattern formed by the arrangement of lens zones of different optical powers is substantially not diffractive. It should be understood that a non diffractive pattern is such that it distributes/spreads the intensity of light passing therethrough in a substantially uniform manner (or in other words does not divert light away from zero order of diffraction), which is contrary to that of a diffraction pattern.

In some embodiments, such non-diffractive pattern can be created by making each of the lens zones of the multi-focal lens of a physical dimension (within the lens plane) much larger than the mean wavelength of light for which the multi-focal lens is designed. The physical dimension of the zones may be larger than the maximal wavelength in a range of wavelength the multi-focal lens is designed for. Each of these lens zones acts as an effective aperture for light passing therethrough. The physical dimension of the lens zone is such that a dimension of the effective aperture defined by the zone substantially does not cause the light to diffract. The term "much larger than the wavelength" used herein refers to a dimension of the order of a few hundred wavelengths or larger. For example, in a multi-focal lens of the present invention used for light of the visible spectrum, the physical dimension of the lens zone may be of a few hundred micrometers.

The non-diffractive pattern in the multi-focal lens region may result from an appropriate combination of refractive and/or diffractive lenses, i.e. a proper arrangement of lens zones being refractive and/or diffractive.

In some embodiments of the invention, the lens zones of different optical functions are arranged on said surface of the lens region in a disordered fashion. Such disordered arrangement may be achieved for example by the zones arranged in random positions forming a net mapped on said multi-focal lens surface, and/or by making said zones with randomly varying geometry (e.g. zone size and/or shape). It should be understood that such disordered fashion arrangement of the lens zones further prevents formation of a diffractive pattern of light passing through the entire net. Indeed, wavefronts passing through spaced-apart zones of the same focal length in said lens region and arriving to a point outside an image plane of said lens accumulate different phases thus preventing formation of an interference pattern (due to the lack of Bragg condition) thus enabling high-contrast imaging. The phase accumulated by wavefronts of different light components passing through spaced-apart zones of the same focal length when arriving to a point within the image plane is substantially equal for all light components, according to Fermat principle, thus allowing image creation.

Preferably, the surface pattern in the lens region is formed by both the surface relief of the lens zones of different optical functions arranged in the above-described relationship along the optical axis of the lens (i.e. spaced from one another a distance larger than the coherence length of passing light) and the above-described disordered fashion arrangement of said zones along said surface of the lens region. Such a "combined" pattern would further decrease diffraction effects due to decoherence of light components passing through lens zones of different optical functions, and due to different phase, accumulated by light passing through the lens zones of the same optical function, at a point outside the image plane of the lens. Preferably, also, the lens zone dimension is too large to cause diffraction effects by itself.

The surface pattern ("combined" or not) can present an optical mask formed by regions of different optical functions. The mask may be integral with the lens region, i.e. by appropriate etching of spaced-apart locations within the lens region. Alternatively, or additionally, an optical mask may be designed to be mounted on / attached to the lens region, or generally in some application (typically, not-ophthalmic) located before or after the lens close thereto. The optical mask (embedded in the lens or attached thereto) may comprise two or more features of different optical functions arranged and configured as described above. For example, the mask may include spaced-apart regions of certain one or more non-zero optical powers spaced by regions of zero-optical power, and thus when applied to a lens with to given optical power adds said one or more optical powers to that of the lens.

Thus, according to one broad aspect of the invention, there is provided an imaging lens structure comprising a lens region defining an effective aperture of the lens structure, said lens region comprising an arrangement of lens zones distributed within the lens region and comprising zones of at least two different optical functions differently affecting light passing therethrough, said zones of at least two different optical functions being arranged in an interlaced fashion along said lens region corresponding to a surface relief of the lens region such that adjacent lens zones of different optical functions are spaced apart from one another along an optical axis of the lens structure a distance larger than a coherence length of light at least one spectral range for which said lens structure is designed.

The arrangement of the lens zones lens region may define two or more different patterns differently affecting light passing therethrough. The features of these different patterns are arranged in the interlaced fashion forming said surface relief.

The interlaced arrangement of the lens zones of said at least two different optical functions may be a disordered arrangement, e.g. a random fashion.

At least some of the lens zones may have a dimension along the surface of the lens region larger than a wavelength of light within said spectral range.

The lens structure described above may have a base lens having a certain first optical function and an optical mask formed by a plurality of lens zones having at least one second optical function. The optical mask is aligned with at least a part of the base lens thereby defining said lens region formed by the lens zones of at least two different optical functions.

The mask may be a separate element attached or located close to the base lens; or may be embedded in the base lens, e.g. in the form of the surface relief etched in said base lens.

In some embodiments, at least one of said at least two different optical function defines a focal length. The lens zones of said at least one optical function defining the focal length may be formed by segments of at least one or refractive lens; or the lens zones of the different focal lengths may be formed by segments of refractive and diffractive lenses.

The above-described imaging lens structure may form a multi-focal ophthalmic lens.

In the above-described imaging lens structure, the lens zones may be configured as angular segments of the lens region arranged around the optical axis. The angular segments may include segments of two different focal lengths arranged in the interlaced fashion; these two different focal lengths may correspond to patient's prescribed far and near vision respectively.

The lens zones of the two different focal lengths are preferably arranged around the optical axis with radial symmetry.

The angular segments of the different focal lengths are preferably arranged such that the angular segments of the same focal length comprise segments arranged along two perpendicular axes, thereby enabling to orient the imaging lens structure with respect to a line of sight such that vertically and horizontally oriented segments within the lens region are those having the focal length corresponding to the near field vision, and the angular segment of other orientations with respect to the line of sight are those corresponding to the far field vision.

Preferably, the imaging lens structure with the angular segments corresponding to the at least two different focal length is equipped with a phase coder comprising at least first and second phase coding patterns associated with said at least two different focal lengths respectively to provide extended depth of focus for imaging via said angular segments. The phase coder may be a separate phase mask located close to or attached to the lens region along the optical axis; or may be a phase mask integral with the lens region.

According to another broad aspect of the invention, there is provided an imaging lens structure comprising a multi-focal lens region comprising a plurality of lens zones of at least two different focal lengths, said lens zones being arranged in an interlaced fashion within a surface of said multi-focal lens region such that the lens zone of one focal length is surrounded by lens zones of one or more different focal lengths and the lens zones of the same focal length are arranged on said surface in an disordered fashion.

According to yet further broad aspect of the invention, there is provided an imaging method comprising passing light through a pattern formed by a plurality of lens zones of at least two different optical functions features of said pattern being spaced from one another along at least an axis of light propagation such as to reduce formation of diffraction and interference effects in at least one imaging plane.

According to yet another broad aspect of the invention, there is provided an imaging lens unit comprising a multi-focal lens region, said lens region comprising: a plurality of angular segments of at least two different focal lengths arranged in a radial symmetry around an optical axis of said lens region, and a phase coder comprising at least two phase coding patterns associated with the angular segments of said at least two different focal lengths respectively, the angular segments of said at least two different focal lengths being arranged such that the angular segments of one focal length comprise segments arranged along two perpendicular axes, thereby enabling to orient the imaging lens structure with respect to a line of sight such that vertically and horizontally oriented segments within the lens region are those having said one focal length.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
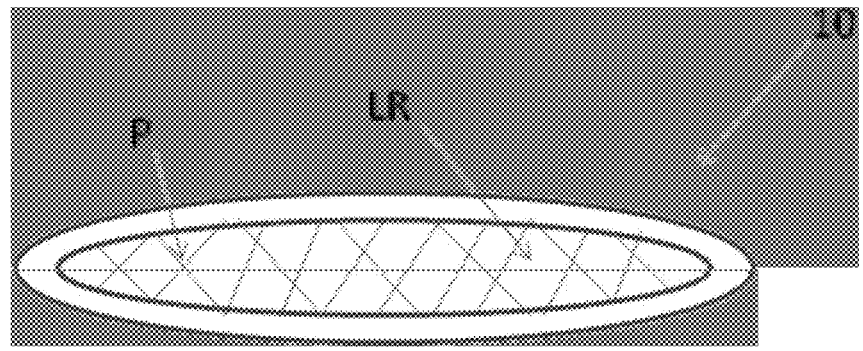
FIG. 1 schematically exemplifies a multi-focal lens according to the present invention.

Reference is made to FIG. 1 illustrating an imaging lens 10 according to the present invention. The imaging lens 10 defines an optical axis, and has a lens region LR that is configured to apply an aperture coding to light passing therethrough. According to the present invention, the aperture coding is aimed at applying to the input light two or more optical functions which differently affect the same property of the light, e.g. focus light from objects at different distances onto the same image plane, and/or apply different phase coding to the light. Thus, the lens region LR may have one or more focal lengths, and may be formed by diffractive and/or refractive lenses.

The different optical functions may be implemented in the lens region LR by applying to the lens region an appropriate pattern P. The pattern P can be in the form of a certain surface relief in a surface of the lens region, which is a combination (or multiplex) of two or more surface profiles, each corresponding to one or more of said optical functions.

More specifically, the present invention is used with multi-focal imaging lenses and is therefore described below with respect to this specific application. However, it should be noted that the general principles of the invention are not limited to this specific application, and the optical function may be other than focusing (i.e. defined by a focal length parameter). For example, the imaging lens of the present invention may include a single-focus lens region carrying the pattern in the form of a multiplex of two or more different phase codes. The term "focal length" is therefore used herein for simplicity; this term is to be interpreted broadly to constitute a parameter describing a specific optical function.

Turning back to FIG. 1, the imaging lens 10 has the multi-focal lens region LR comprising a plurality of lens zones. The plurality of lens zones may contain lens zones of different focal lengths, or a combination of lens zones of different focal lengths with phase coding. The plurality of lens zones of different focal lengths are arranged in an interlaced pattern P formed on the surface of the lens region LR.

The arrangement of the lens zones of different optical functions (e.g. focal lengths) is such as to prevent interference of light components passing through locally adjacent lens zones of different optical functions and thus not impeding the imaging process. Alternatively or additionally, the arrangement of the lens zones of different optical functions (e.g. focal lengths) is such as to prevent interference of light components passing through the lens zones of the same optical function, and thus again not impede the imaging. These effects will be described more specifically further below.

Also, preferably, the lens zones are configured to prevent diffraction of light passing through each of the lens zones. To this end, each lens zone is of a physical dimension (along the lens surface) much larger than a mean wavelength within a wavelength range of light for which the lens region is designed. The lens zone, which defines an effective aperture, is much larger than the wavelength and therefore substantially does not diffract the light. Thus, the interlaced pattern is set to be substantially non diffractive in the meaning that light passing through the lens is spread in a uniform manner and does not divert light away from zero order of diffraction.

It should be understood that the multi-focal lens of the invention, implemented as either one of the examples described herein, can be an integral structure formed by a net of different lens zones embedded in a lens region (e.g. in the form of a surface relief) or may be formed by a mask placed on top of or close to the lens region of a lens. If the multi-focal lens structure utilizes a separate mask, the latter may be configured such that only zones of one group has an optical power adding to that of the lens, while those of the other group have no optical power.

Figure 2:
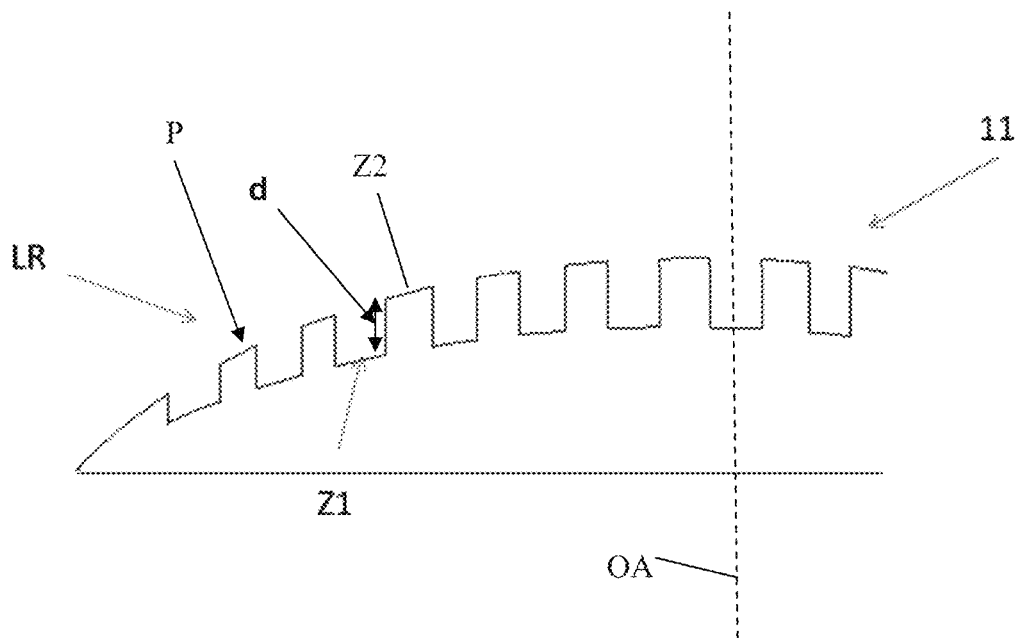
FIG. 2 is an example of surface relief formed on a multi-focal lens region as presented in the current invention.

As indicated above, according to some embodiments of the invention, the interlaced pattern P is formed as a surface relief on a surface of the lens region LR. In this connection, reference is made to FIG. 2 showing more specifically the pattern P formed within the lens region LR. In order to prevent interference of light components passing through the locally adjacent lens zones, Z1 and Z2, of different optical functions (defining different focal lengths), the pattern P is such that these lens zones Z1 and Z2 are spaced-apart along an optical axis OA of the lens region LR a distance d which is higher than a coherence length of light in the wavelength range for which the multi-focal lens region has been designed, e.g. visible range. The light components passed through the locally adjacent lens zones Z1 and Z2 spaced apart along the optical axis a distance larger than the coherence lengths will not be phase correlated and therefore will effectively add at an image plane of the lens region in intensity and not in field. Uncorrelated wavefronts, which effectively add in intensity substantially does not create an interference pattern but typically form a light spot.

As indicated above, the coherence length, $\Delta Z$, of a light source is defined as follows:

$$\Delta Z = \frac{c}{n\Delta v} = \frac{\lambda^2}{\Delta \lambda} \quad (1)$$

where c is the speed of light, n is the refraction index of media in which the light propagates, $\lambda$ is the central wavelength for which the element is designed, $\Delta \lambda$ is the bandwidth of wavelengths, and $\Delta v$ is the spectral bandwidth of the light source. For light of the visible spectrum, the bandwidth is relatively large and the coherence length is typically less than 1 micron. The coherence length of white light is basically in the order of the mean wavelength. The distance between adjacent zones, along the optical axis, can therefore be of the order of several microns.

Turning back to FIG. 2, the lens region LR may be a bi-focal lens. The pattern P is formed as a surface relief on the lens' surface 11. The zones Z1 and Z2 of two different focal lengths f1 and f2 are arranged in an interlaced fashion within the lens surface, and are arranged in a spaced-apart relationship along the optical axis OA of the lens such that the distance d between the locally adjacent lens zones Z1 and Z2 of different focal length is higher than a coherence length of light of wavelength range for which the lens is designed. For example, the distance d can be of about a millimeter, or of about few hundreds of microns.

Such lens region LR as exemplified in FIG. 2 can provide imaging of an object onto two or more different image planes at distances determined by the two or more focal lengths respectively, or can provide imaging of different objects, standing at different distances from the lens, on to the same image plane. For example, light which passes through zones Z1 of the lens region will produce an image of an object standing at a distance fitting f1 focal length at the image plane, while light which passes through zones Z2 will produce an image of object standing at a distance fitting f2 focal length onto the same image plane. At the image plane, the light components that have passed through the locally adjacent zones of different foci add in intensity rather than in field due to decoherence of the light components.

Preferably, as will be exemplified below, the lens zones of different focal lengths may be arranged in a disordered fashion. This disordered (e.g. random or a-periodic) arrangement of the lens zones within the surface of the lens region may be used in addition to the above-described spaced-apart arrangement along the optical axis of the lens region. If the lens zones of different focal lengths are arranged in a disordered fashion, this disordered arrangement of the lens zones would eliminate or at least significantly reduce formation of interference, which would otherwise appear resulting from effects (such as Bragg diffraction) caused from light passing through a periodic pattern.

Considering the lens zones' net in the form of a surface relief on the surface of the lens region (e.g. the arrangement of FIG. 2), the following should be noted. In some ophthalmic application it is necessary that the surface of an ophthalmic lens is flat in order to avoid stimulation of the eye. For this purpose, the surface of the lens zones' pattern may be covered with a transparent substrate in order to fill the gaps along the optical axis. The transparent substrate is appropriately selected for a given lens, such that its effects (e.g. optical power) on the focal lengths of the multi-focal lens are compensated by chosen focal lengths of the different lens zones of the lens.

In order to form an arrangement of lens zones of different optical functions, e.g. focal lengths, several (at least two) different lenses can be appropriately combined in a certain spatial arrangement. For example, let us consider the case of designing a bi-focal lens region, where one lens has optical power corresponding to 57 diopters (focal length of 17.5 mm) and the other lens has optical power corresponding to 59.5 diopters (focal length of 16.8 mm) Each of these two lenses is divided into multiple zones, and the so-obtained two groups of different zones are distributed in an interlaced fashion, e.g. both groups including the same number of zones. The lens zones may have any geometries (rectangles, triangles, etc.), similar or not. Each spatial segment of the lens region is randomly occupied with a lens zone of the first group (first lens) or of the second group (second lens). As a result, a lens region of the so-obtained "combined" multi-focal lens has a portion (formed by discrete zones) occupied by the first lens and the rest occupied by the second lens.

It should be understood that a similar lens region can be obtained by using a base lens of one focal length and creating/placing on a surface thereof a mask formed by spaced-apart regions/zones of one or more other lens of different focal length(s). For example, in order to obtain a lens having the above-mentioned bi-focal lens region, i.e. 57 and 59.5 diopters, a lens with the optical power corresponding to 58 diopters can be used as a base lens and a mask formed by discrete segments of two lenses: a focusing lens of 1.5 diopters and a diffusing lens of (−1) diopters. Also, a base lens may be selected to have an optical power corresponding to 57 diopters and add a mask formed by spaced-apart zones of a lens with the optical power of 2.5 diopters spaced by zones of zero optical power, i.e. thus resulting in zones of the optical power of the base lens (i.e. 57 diopters).

The following is an example of simulating the design of a bi-focal lens with the above parameters, i.e. having zones of optical power corresponding to 57 diopters (focal length of 17.5 mm) and zones of optical power corresponding to 59.5 diopters (focal length of 16.8 mm) It should be noted, although not specifically shown, that this embodiment may or may not be combined with the principles of the embodiment of FIG. 2 (i.e. spaced-apart arrangement of the lens zones along the optical axis of the lens with a distance larger than coherence length).

Figure 3A:
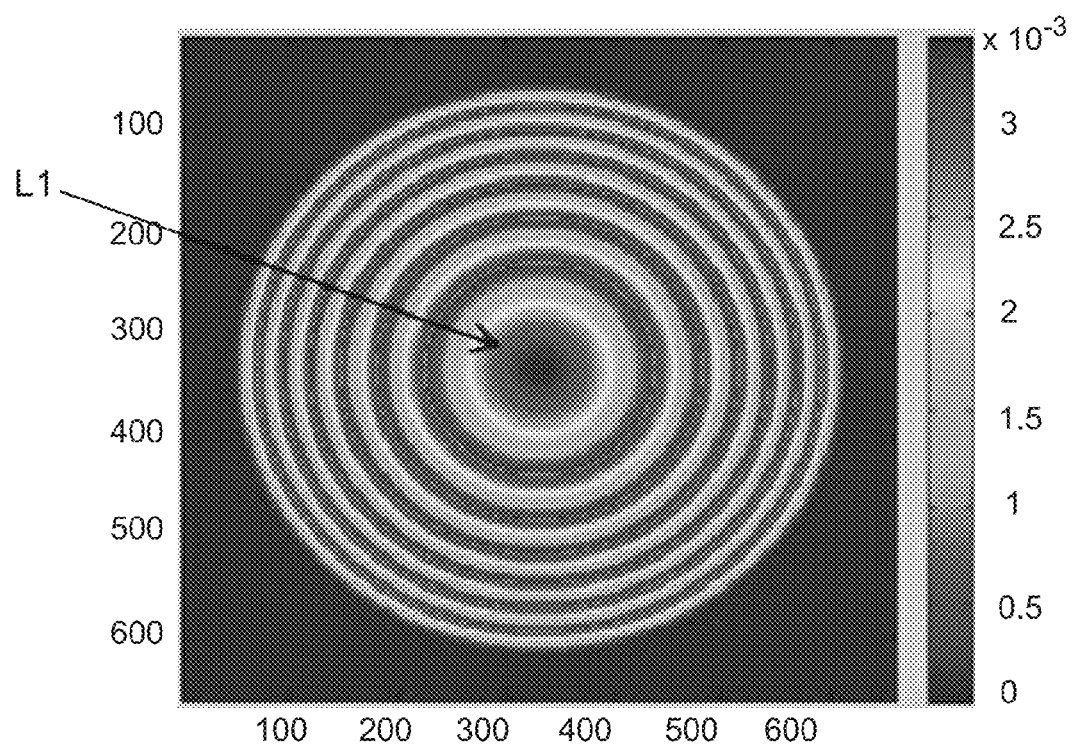
FIGS. 3A to 3D show simulation procedure and result for a bi-focal lens structure of the present invention, where different focal length zones are randomly ordered in a lens region.

In this example, a refractive base lens is selected with the optical power corresponding to 57 diopters, and then a mask is formed thereon from segments of a diffractive lens having optical power of 2.5 diopters. The simulation procedure and results are illustrated in FIGS. 3A to 3D. FIG. 3A shows the surface curvature of a diffractive lens L1 corresponding to 2.5 diopters optical power and having focal length f1. It should be understood that the gray level pattern corresponds to the variation of the lens thickness (height) in accordance with the curvature. This lens L1 can be divided into multiple segments of different or same dimensions and/or shapes, and these segments be then placed onto the base lens in a disordered fashion spaced-apart by segments of the base lens (or for example by segment of another transparent substrate of zero optical power). Thus, the bi-focal lens region LR is created from the base lens carrying a map of randomly multiplexed geometrical zones of lens L1 spaced by zones of the base lens. In some embodiments the spaces between lens L1 zones are presented by a simple transparent plate with no optical power.

Figure 3B:
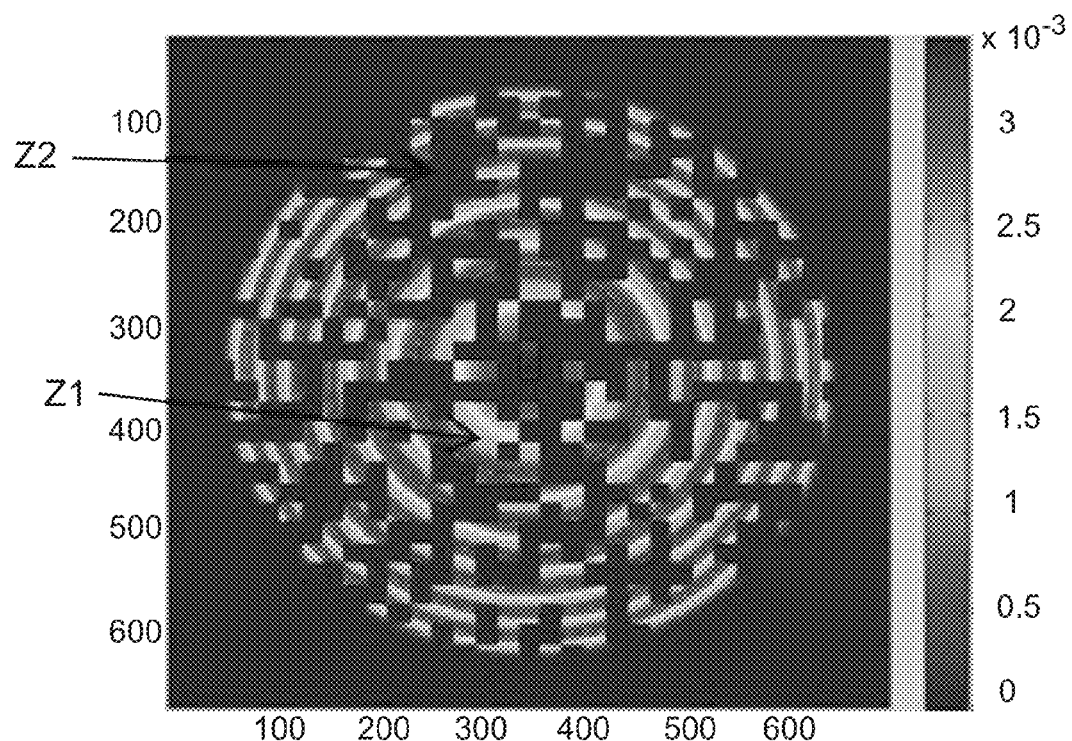
Figure 3C:
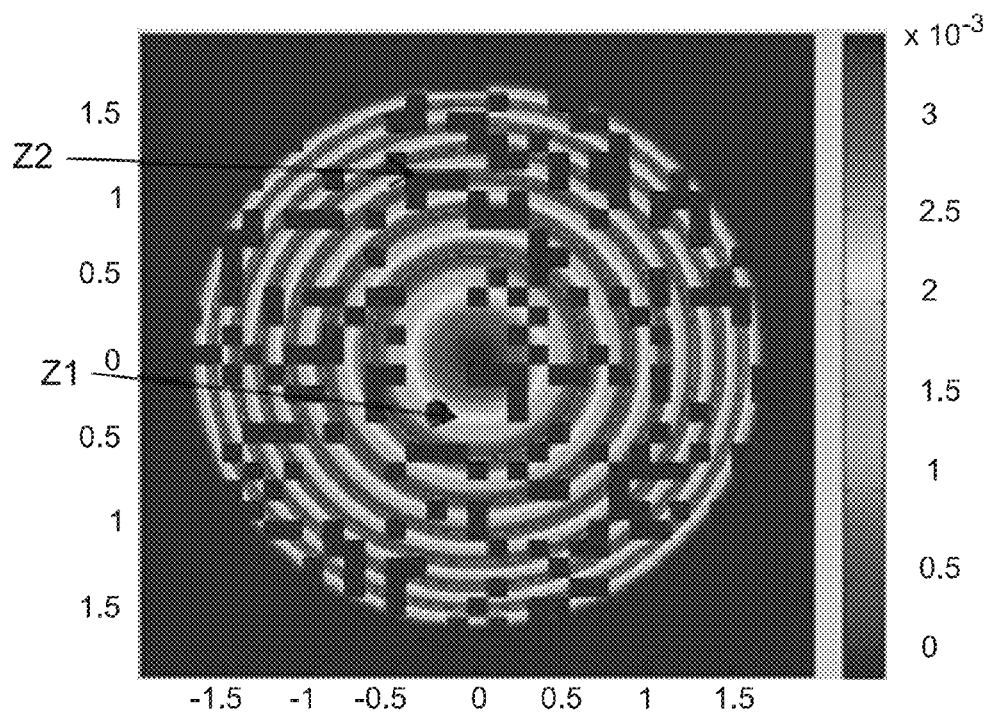

FIGS. 3B and 3C show two examples of a mask formed by randomly distributed discrete segments Z1 of lens L1 placed on and thus spaced by a transparent zero-power substrate Z2. Thus, the mask is a pattern of lens zones of certain focal length f1 (or generally n different focal lengths) arranged in a spaced-apart interlaced fashion. Here, the interlaced fashion is implemented by disordered or a-periodic (e.g. random) distribution of the lens zones. Such disordered (random) arrangement of the lens zones eliminates, or at least substantially reduces, diffraction effects of the lens as described above.

The mask pattern thus corresponds to a non-diffractive lens. The number of focal lengths in the mask, or in the entire lens region obtained by placing the mask onto a base lens, and the focal length values may correspond to the optical power distribution for far- and near-vision as prescribed for a specific patient. The disordered fashion of the lens zones is aimed at decreasing interference formed by interaction of light components passing through the spaced-apart lens zones of the same focal length. The optical paths for interacting light components coming from different zones of the same focal length are different, and accordingly the phase accumulated by these light components is different. Therefore, there is no full constructive of destructive interference of the interacting light components for any point other than the focal point, i.e. the point in an image plane. The fact that the lens zones are arranged in an a-periodic fashion reduces diffraction patterns, such as Bragg diffraction, caused and enhanced by periodic structures.

As indicated above, the disordered-pattern lens region can be created by dividing said lens region into zones. Each of said zones is treated to provide a certain focal length according to a random variable with a distribution selected such that it satisfies a desired fill factor of the lens for said focal length. The desired fill factor may be such that light intensity is divided between the two or more optical powers evenly, or such that one optical power will affect larger portion of the light intensity than one or more other optical powers. FIGS. 3B and 3C show two examples of the disordered-pattern lens region (masks) with different fill factors, respectively. In the figures, zones Z1 correspond to regions of the lens with focal length f1, and zones Z2 correspond to regions of no optical power. When such mask is placed in a base lens of focal length f2 (not shown here), these regions Z2 would correspond to those of focal length f2. Thus, the net of lens zones (i.e. pattern on the lens surface) in a so-obtained combined lens region has two groups, one group including spaced-apart disordered arrangement of zones Z1 and the other group including disordered distribution of lens zones Z2. In this simulation, the lens zones Z1 are zones of a diffractive lens with focal length f1, while lens zones Z2 are parts which would be aligned with a refractive lens with focal length f2. FIG. 3B shows a lens in which the lens zones having different focal lengths are distributed randomly but evenly along the lens region, in a way that the fill factor of the bi-focal lens is 50:50. This means that half of the optical energy passing through the lens region is transferred through zones Z1 and half of the energy is transferred through zones Z2. This provides for a bi-focal (generally multi-focal) lens where the transmitted energy is evenly divided between the two (or generally two or more) optical powers of the lens. FIG. 3C shows a lens region in which the fill factor is 70:30. The lens zones are arranged such that 70 percent of the area of the bi-focal lens is covered by zones Z1, and 30 percent is covered by zones Z2, in a way that most of the energy is collected from the object plane by Z1 lens zones' group, rather than being distributed evenly between the groups.

In the preferred embodiment of present invention a plurality of lens zones are formed as a surface relief on the surface of a multi-focal lens region. The surface relief is such that the lens zones are also arranged in the above described disordered interlaced pattern and also the lens zones of the different focal lengths are spaced-apart along the optical axis of the lens a distance higher than a coherence length of light at a wavelength range for which the lens is designed. This arrangement provides that light passing through zones of different focal lengths is not phase correlated, and the disordered fashion of the lens zones of the same focal length decreases interference effects.

Figure 3D:
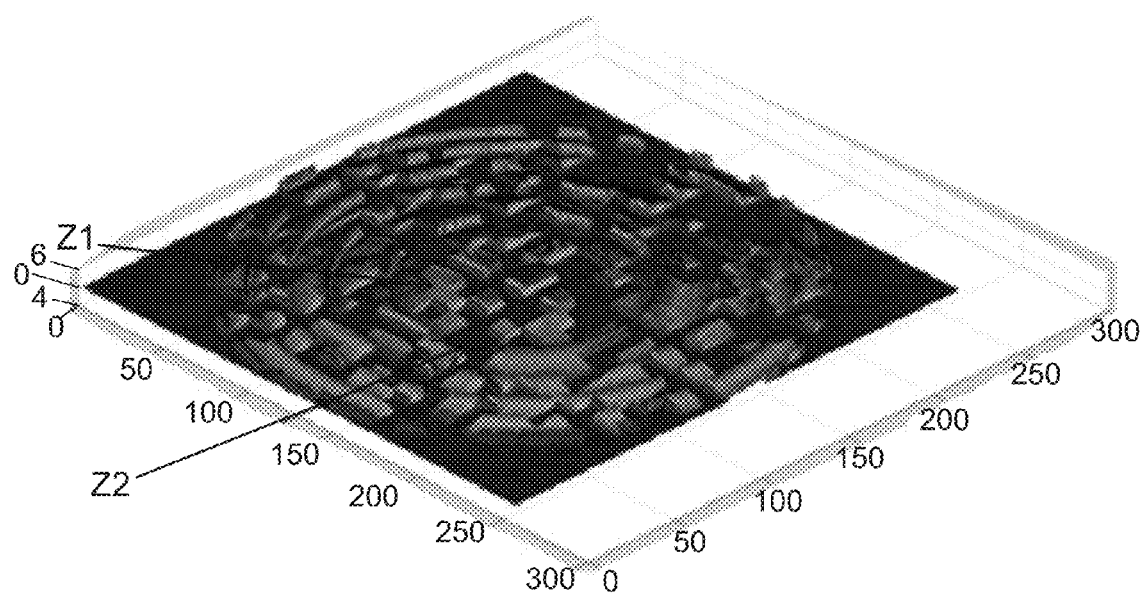

FIG. 3D illustrates a 3-dimensional view of the optical mask of FIG. 3B to be placed on a lens region of a base lens (not shown). The mask is configured from random arrangement of lens zones Z1 and Z2. In this figure, zones Z1 are zones of a refractive lens L1 with focal length f1, and zones Z2 are those of an optically transparent substrate having no optical power. As shown in the figure, the arrangement of the lens zones Z1 is in the form of a surface relief such that they are spaced from one another by zones Z2 along the surface of the substrate and also such that zones Z1 and Z2 are spaced along an optical axis of the lens L1. Preferably, this distance along the optical axis is larger than a coherence length of light as described above. For a visible spectrum, the distance along the optical axis is to be larger than 0.5 or 1 micrometer. The distance may be of the order of several micrometer, and it may be as large as some hundreds of micrometers. The multi-focal lens mask shown in FIG. 3D can be placed on the surface of a single-focus base lens to provide a multi-focal lens arrangement.

Reference is now made to FIGS. 4A to 6C showing simulation results for the above-described multi-focal lens arrangement where the mask of FIG. 3E formed by segments of a diffractive lens with optical power of 2.5 diopters is placed on top of an "ideal" single-focus lens with focal length of 17.5 mm. The combined lens arrangement forms a multi-focal lens region with focal lengths of 17.5 mm and 16.8 mm.

Figure 4A:
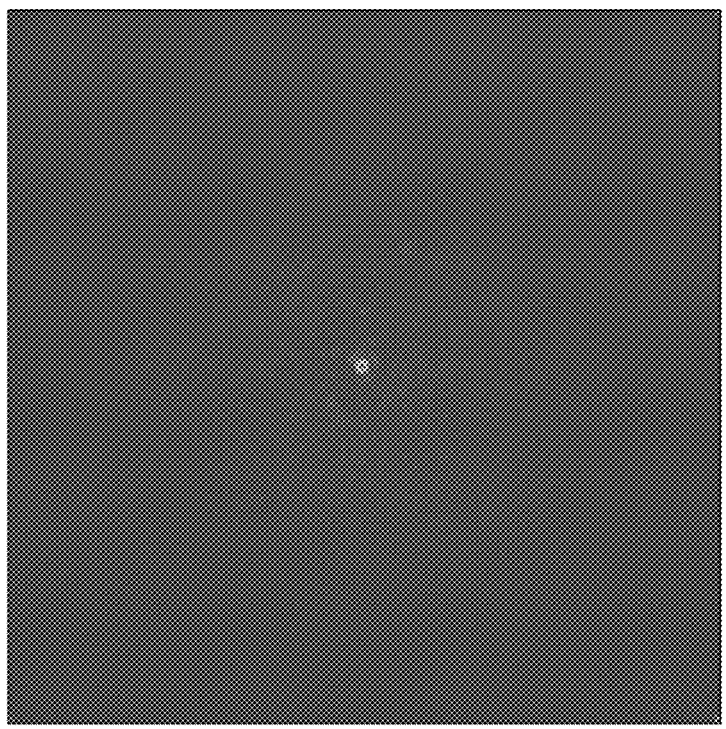
FIGS. 4A-4C show simulation results for the measurements of point spread function of the lens structure of FIG. 3B measured in near-, medium- and far-field respectively of the lens.
Figure 4B:
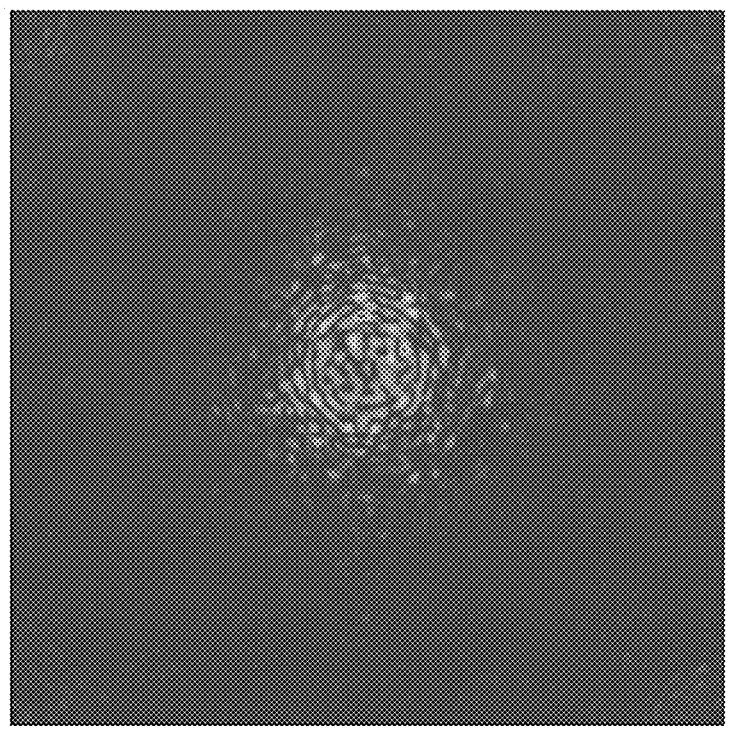
Figure 4C:
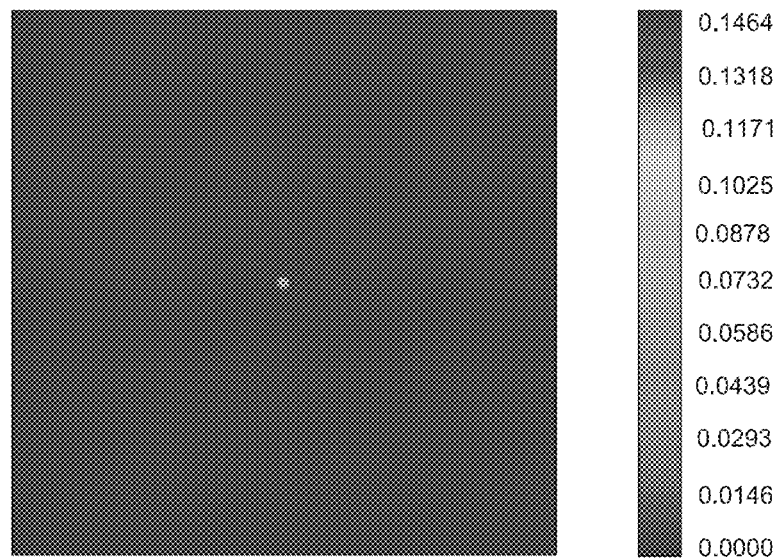

FIGS. 4A to 4C show point spread function (PSF) measurements for the multi-focal lens arrangement. The figures show PSF of the lens arrangement for near field (FIG. 4A, 410 mm), intermediate distance field (FIG. 4B, 850 mm) and far field (FIG. 4C) distances from the lens. These figures actually present imaging a point-like light source located at different distances from the multi-focal imaging lens arrangement. As shown in FIGS. 4A and 4C, for both the near field distances and the far field distances the lens arrangement provides an in-focus image of the point-like light source. However, FIG. 4B shows that at some distances from the lens an object might be seen out of focus. Moreover, in all three figures, no diffraction or interference patterns are observed. Such patterns might have been caused by a periodic arrangement of the different lens zones along the lens region.

Figure 5A:
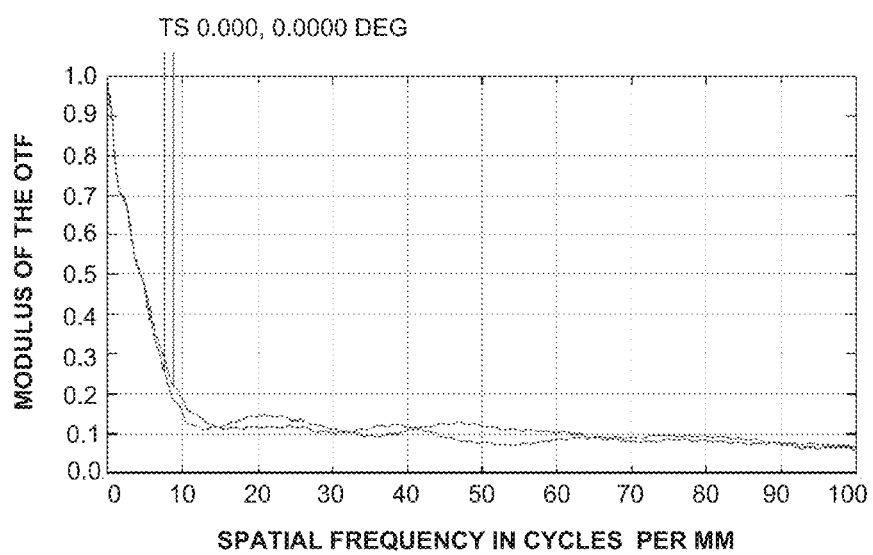
FIGS. 5A-5C show simulation results for a Modulation Transfer Function (MTF) of the lens structure of FIG. 3B, in near-, medium- and far-field respectively of the lens.
Figure 5B:
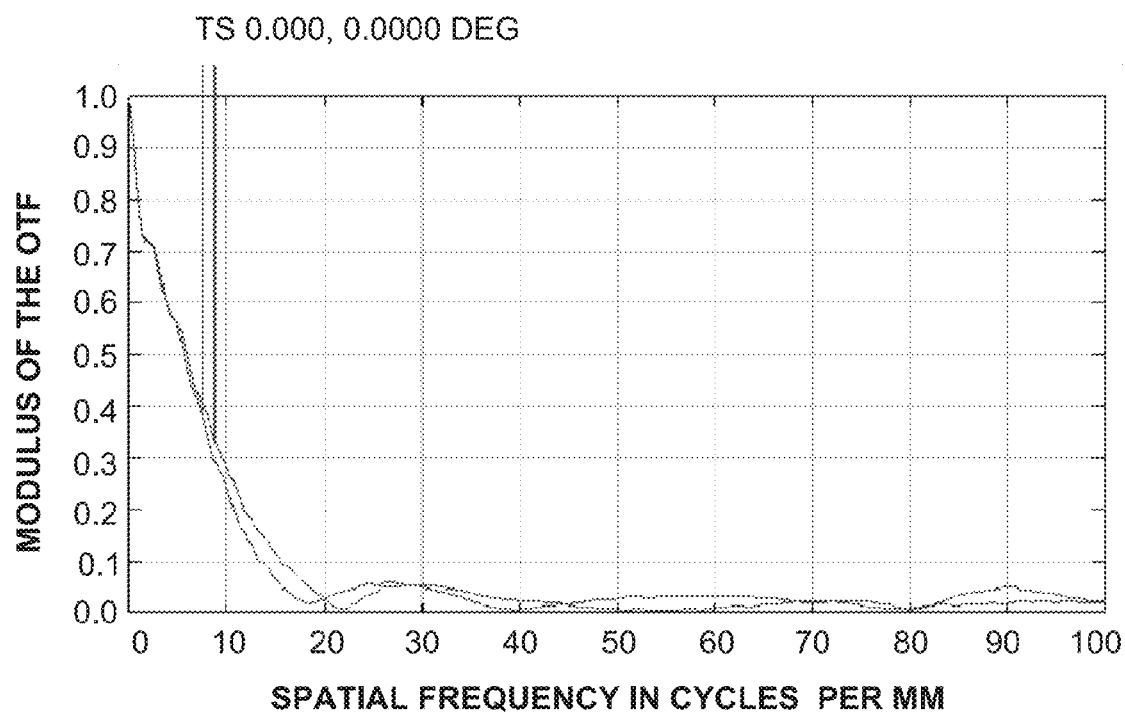
Figure 5C:
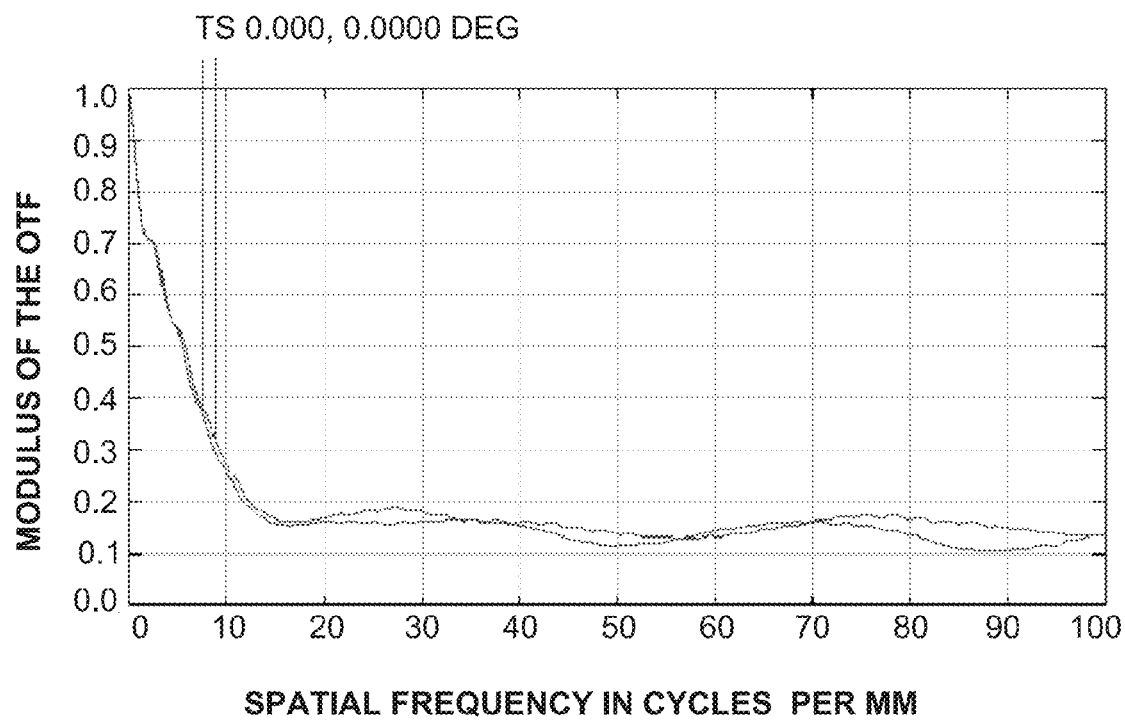

FIGS. 5A to 5C show modulation transfer function (MTF) measurements of a point-source image located at the near field distance (FIG. 5A, 410 mm), intermediate distance (FIG. 5B, 850 mm) and far field distance (FIG. 5C) from the lens arrangement. It can be seen from FIGS. 5A and 5C, that the MTF corresponding to either one of the focal planes of the lens arrangement has absolute values of 0.1-0.2 at spatial frequencies of above 20 cycles per millimeter. An MTF value higher than 0.1 corresponds to imaging with visible contrast and signifies that such image is sharp enough for a person to distinguish 20 lines or more within a millimeter. FIG. 5B shows that for spatial frequencies above 20 cycles per millimeter, the MTF values are below 0.05. Such a drop in the MTF values results with an out-of-focus image, while wide spread of higher values of the MTF results in a sharp in-focus image. This corresponds to a behavior of a bi-focal lens.

Figure 6A:
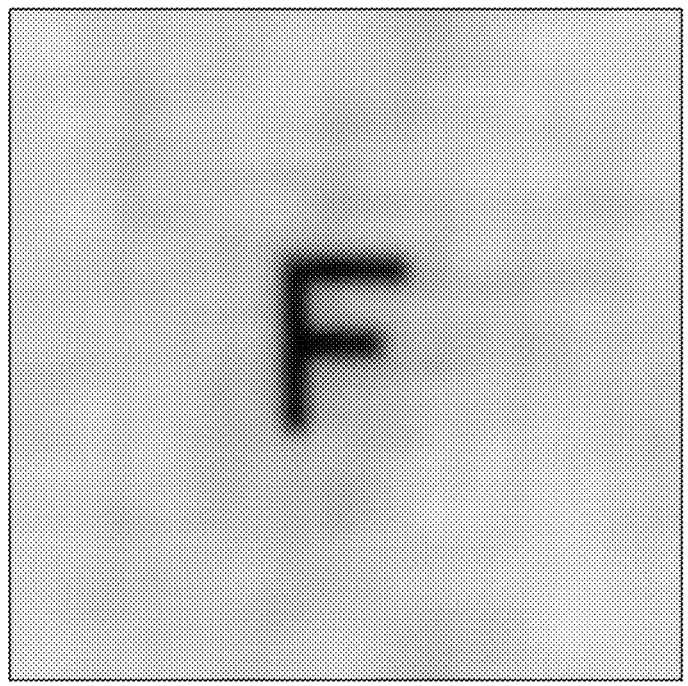
FIGS. 6A-6C show simulation results of imaging of an object with resolution of 100 line-pairs/mm using the lens structure of FIG. 3B in near-, medium- and far-field respectively of the lens.
Figure 6A:
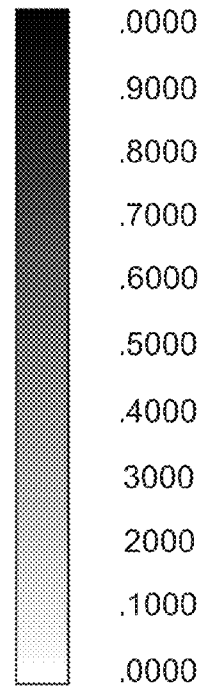
Figure 6B:
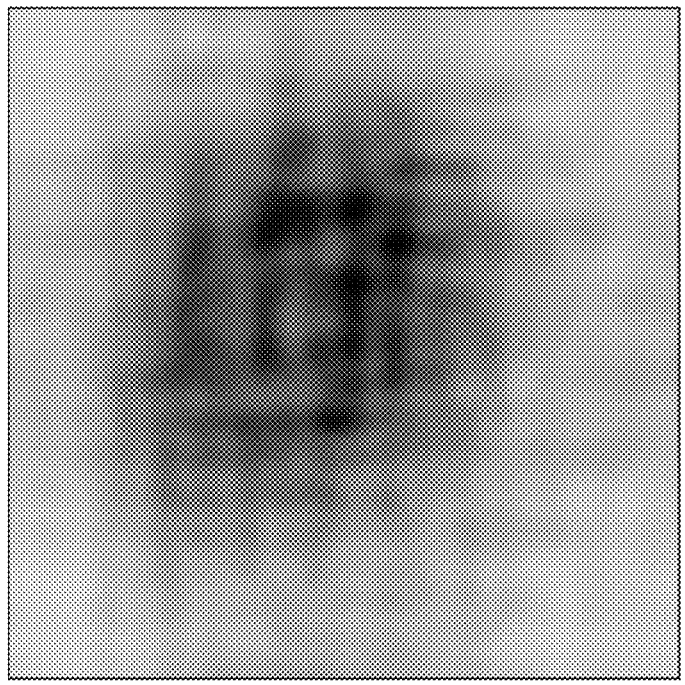
Figure 6B:
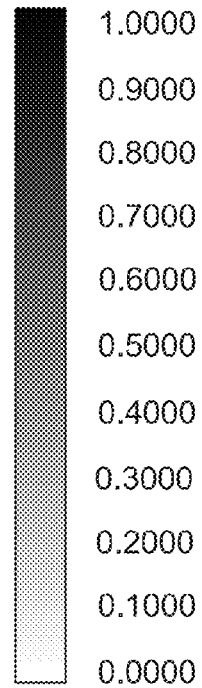
Figure 6C:
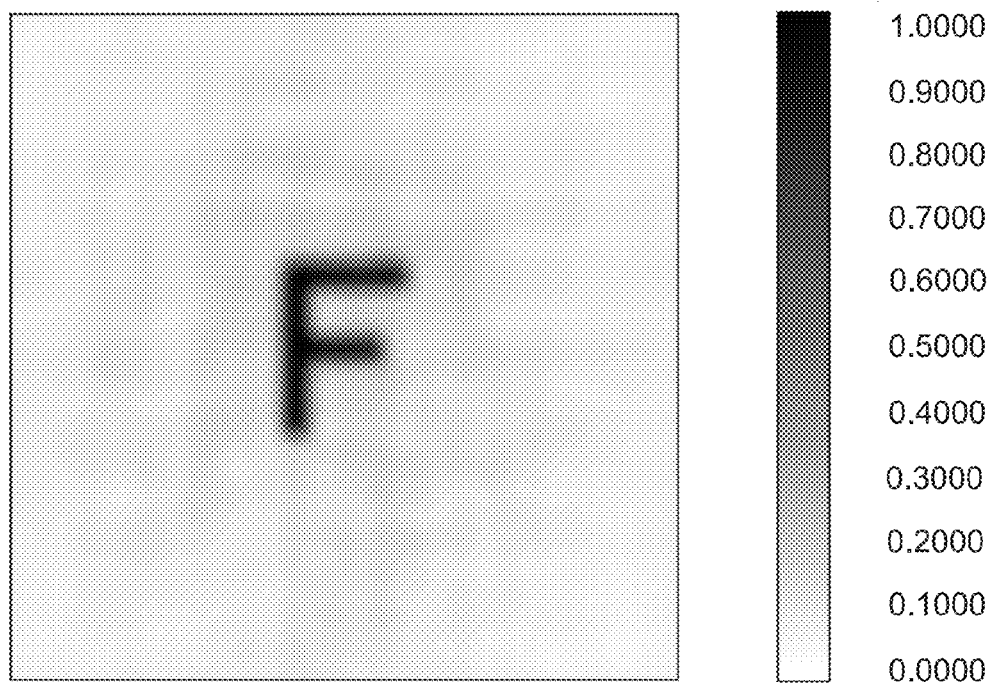

FIGS. 6A to 6C show three images of an object obtained using the bi-focal imaging lens described above. The object is set at a resolution of 100 line-pairs per millimeter, presenting the object's highest spatial frequency, and is located at a near field distance (FIG. 6A, 410 mm), intermediate field distance (FIG. 6B, 850 mm) and far field distance (FIG. 6C) from the imaging lens. As can be seen from FIGS. 6A and 6C, the imaging lens arrangement of the invention provides high contrast imaging and an in focus image for both near- and far-field objects. FIG. 6B shows an out of focus image of the object, which is now located in a distance between the correct distances relating to any of the focal lengths of the lens arrangement.

Figure 7:
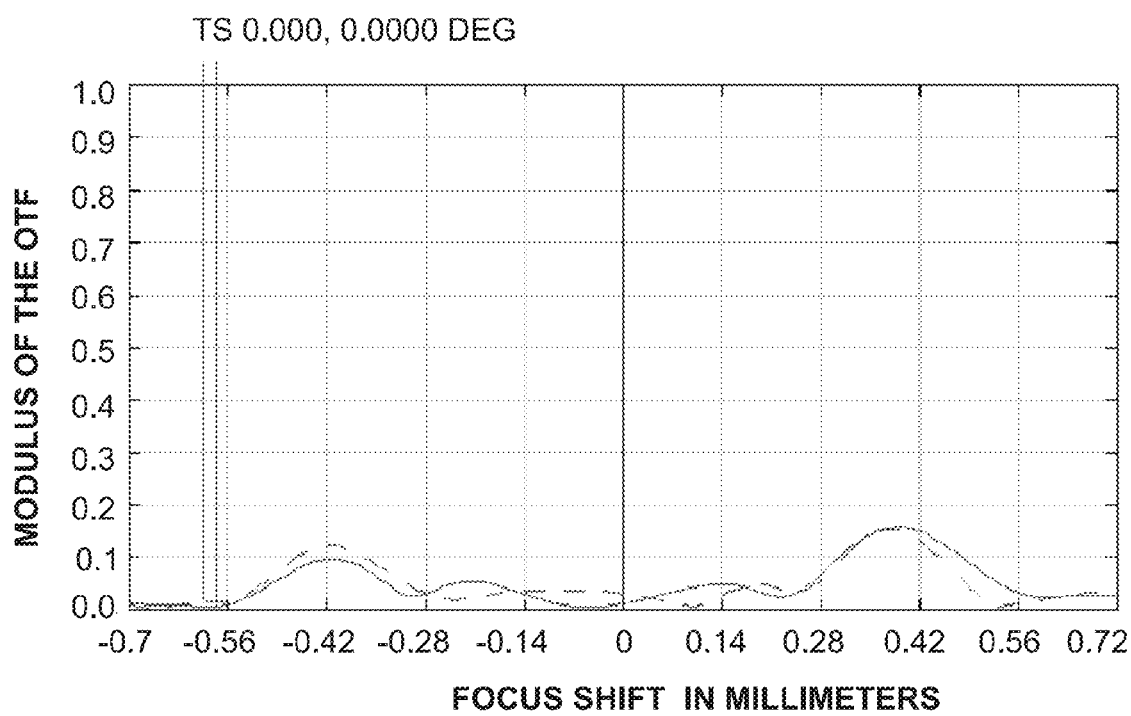
FIG. 7 shows through focus measurement of MTF of the lens structure of FIG. 3B.

Reference is now made to FIG. 7, showing a through focus measurement of MTF (TFMTF) of the lens arrangement described above. This measurement presents the multi-focal nature of the lens arrangement of the present invention by presenting two focal planes at the relevant distances from the lens. The two focal planes can be seen as two hills in the graph, located at around −0.41 and 0.35. The numbering of the x-axis in the graph stands for a shift of the detector plane and represents focal lengths of 16.8 and 17.5 millimeter.

Figure 8A:
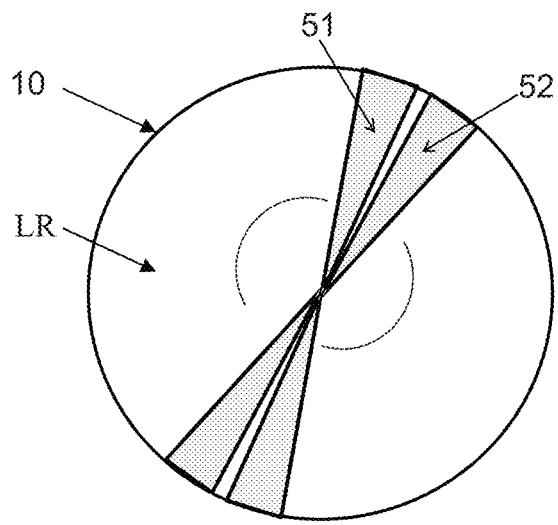
FIG. 8A shows a multi-focal imaging lens having angular segments with different focal length.

According to some embodiments of the invention, the lens region is segmented into angular segments having different focal lengths, e.g. of at least two different focal lengths. Reference is made to FIG. 8A illustrating an example of such a multi-focal lens structure 10 having a lens region LR formed by angular segments of different focal length, two such angular segments 51 and 52 having focal lengths f1 and f2 being shown in the figure. In some embodiments, the different focal lengths correspond to near- and far-field vision as prescribed for a patient.

In order to improve adaptation processes in a human's brain, the angular segments of the different focal lengths are arranged in an interlaced fashion, and also preferably with radial symmetry. The brain process can prefer image data of certain angular orientation and suppress data of other angular orientation, thus allow sharp imaging of images from different object planes. Hence, preferably, the angular slices of the lens region LR having different focal lengths are arranged such that the angular segments/slices of the same focal lengths include segments arranged along two perpendicular axes. With such arrangement, the lens region can be appropriately oriented with respect to a line of site (coinciding with the optical axis when the lens structure is in operation, e.g. being a contact or intraocular lens), the angular segment corresponding to the near-field vision are oriented along vertical and horizontal axes, while segments having other angular orientations with respect to the line of site are those used for far field distances. This configuration is aimed at providing sharp imaging of text or other printed images at close range to the eye, keeping in mind that remote images typically correspond to natural scenes where the dominant axes are not necessarily the vertical and horizontal ones.

The lens region may be segmented to 8 angular regions, i.e. each region correspond to 45 degrees, where 4 regions, that are to be aligned with the horizontal and vertical axes, are configured with focal length for near-field imaging and the other 4 regions are configured for far-field imaging. The lens region may be segmented to 16 angular regions, or any other number of segments covering the entire angular range of the lens.

Figure 8B:
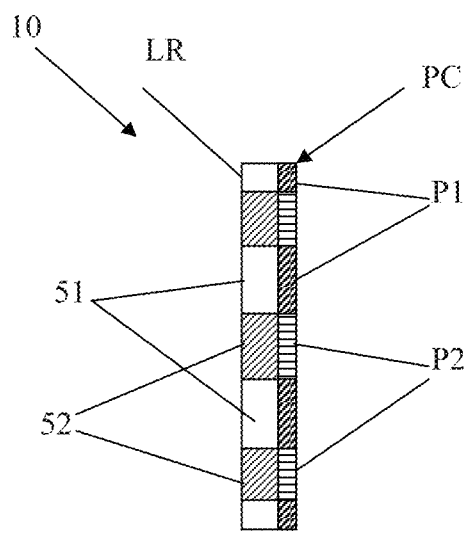
FIG. 8B shows an example of a multi-focal imaging lens structure of FIG. 8A equipped with a phase coder for providing extended depth of focus.

Preferably, such angular segments containing lens region is associated with a phase coder configured for extending the depth of focus for imaging. The phase coder may generally include a single phase coding pattern commonly distributed within the different segments of the lens region. Preferably, however, each group of angular segments having the same focal length is associated with a different phase coding pattern of said phase coder for extended depth of focus fitting with the corresponding focal length. This is exemplified in FIG. 8B, showing an imaging lens structure 10 having a lens region LR formed by a plurality of angular segments of two groups 51 and 52 having different focal lengths f1 and f2 and arranged in an interlaced fashion; and a phase coder PC. The latter may be either a separate phase mask located close to or attached to the lens region or a phase mask embedded or integral with the lens region. The phase coder PC includes two or more phase patterns, corresponding to the number of groups of the angular segments in the lens region—two such phase coding patterns P1 and P2 in the present example. Each pattern is formed by one or more phase affecting regions different from that of its surroundings. An example of a suitable phase coding pattern is described in the above-listed patent publications U.S. Pat. Nos. 7,365,917; 7,061,693; US 2009/074239; US 2009/116096; U.S. Pat. No. 7,646,549, all assigned to the assignee of the present application.

For example, the angular segments configured for short-range (near-field) imaging may be associated with the phase coding patter providing extended depth of focus corresponding to 3 diopters (or 5 diopeters, or 2 diopters), while the angular segments having focal length for large distance imaging may be associated with the phase coding pattern corresponding to extended depth of focus for 1 diopters (of ½ diopter, or 2 diopters). This is to enhance the imaging capabilities, since at short-range small variations of the exact distance of an object may result with large variations of the image plane, while at large distances, even large variations of the object plane does not result with movement of the image plane.

Thus, the present invention provides a simple and effective approach for lenses of multiple optical functions, especially multi-focal lenses. The multi-focal approach of the invention is all-optical and easy to implement and can thus be advantageously used in various imaging systems including ophthalmic applications. Those skilled in the art will readily appreciate that various modifications and changes can be applied to the embodiments of the invention as hereinbefore described without departing from its scope defined in and by the appended claims.

The invention claimed is:

1. An imaging lens structure comprising:
a lens region defining an effective aperture of the lens structure, said lens region comprising an arrangement of lens zones distributed within the lens region and comprising zones of at least two different optical functions differently affecting light passing therethrough, said arrangement of lens zones being formed by a surface relief on an outer surface of the lens region, such that the lens zones of the at least two different optical functions are arranged in an interlaced fashion along said lens region and adjacent lens zones of the different optical functions are spaced apart from one another along an optical axis of the lens structure a distance larger than a coherence length of white light illumination; and
a phase coder comprising multiple phase coding patterns associated with the lens zones of the at least two different optical functions.

2. The lens structure of claim 1, wherein said lens region comprises two or more different patterns formed by said arrangement of the lens zones differently affecting light passing therethrough, features of said two or more different patterns being arranged in the interlaced fashion forming said surface relief.

3. The imaging lens structure of claim 1, wherein said lens zones of at least two optical functions are arranged in a disordered fashion.

4. The lens structure of claim 3, wherein said lens zones of at least two optical functions are arranged in a random fashion.

5. The lens structure of claim 1, wherein at least some of the lens zones have a dimension along the surface of the lens region larger than a wavelength of light within a-spectral range for which the lens was designed.

6. The lens structure of claim 1, further comprising a base lens having a certain first optical function and an optical mask formed by a plurality of lens zones having at least one second optical function, said optical mask being aligned with at least a part of the base lens thereby defining said lens region formed by the lens zones of said at least two different optical functions.

7. The lens structure of claim 6, wherein said mask is a separate element attached or located close to the base lens.

8. The lens structure of claim 6, wherein said mask is embedded in the base lens.

9. The lens structure of claim 8, wherein said mask is the surface relief etched in said base lens.

10. The lens structure of claim 1, wherein at least one of said at least two different optical functions defines a focal length.

11. The lens structure of claim 10, wherein the lens zones of said at least one optical function defining the focal length are formed by segments of at least one diffractive lens.

12. The lens structure of claim 10, wherein the lens zones of said at least one optical function defining the focal length are formed by segments of at least one refractive lens.

13. The lens structure of claim 10, wherein said lens zones of the different focal lengths are formed by segments of refractive and diffractive lenses.

14. The imaging lens structure of claim 1, wherein the lens zones are configured as angular segments of the lens region arranged around the optical axis.

15. The imaging lens structure of claim 14, wherein said angular segments comprise segments of two different focal lengths arranged in the interlaced fashion.

16. The imaging lens structure of claim 15, wherein said two different focal lengths corresponding to a patient's prescribed far and near vision respectively.

17. The imaging lens structure of claim 15, wherein the lens zones are associated with the two different focal lengths and are arranged around the optical axis with radial symmetry.

18. The imaging lens structure of claim 17, wherein the angular segments of the different focal lengths are arranged such that the angular segments of the same focal length comprise segments arranged along two perpendicular axes, thereby enabling to orient the imaging lens structure with respect to a line of sight such that vertically and horizontally oriented segments within the lens region are those having the focal length corresponding to the near field vision, and the angular segment of other orientations with respect to the line of sight are those corresponding to the far field vision.

19. The imaging lens structure of claim 15 wherein the phase coder comprises first and second phase coding patterns associated with lens zones of the two different focal lengths respectively to provide extended depth of focus for imaging via said angular segments.

20. The imaging lens of claim 19, wherein the phase coder may have one of the following configuration: (i) is a separate phase mask located close to or attached to the lens region along the optical axis; (ii) is a phase mask integral with the lens region.

21. A multi-focal ophthalmic lens formed by the imaging lens structure of claim 1.

22. The multi-focal ophthalmic lens of claim 21, configured as intraocular lens, intracorneal lens or contact lens.

23. The imaging lens of claim 1, configured for use as spectacles lens.

24. An imaging lens unit comprising a multi-focal lens region, said lens region comprising: a plurality of angular segments of at least two different focal lengths arranged in a radial symmetry around an optical axis of said lens region, and a phase coder comprising at least two phase coding patterns associated with the angular segments of said at least two different focal lengths respectively, the angular segments of said at least two different focal lengths being arranged such that the angular segments of one focal length comprise segments arranged along two perpendicular axes, thereby enabling orientation of the imaging lens structure with respect to a line of sight such that vertically and horizontally oriented segments within the lens region are those having said one focal length.

25. The imaging lens unit of claim 24, wherein said two different focal lengths corresponding to patient's prescribed far and near vision respectively.

26. The imaging lens unit of claim 25, wherein the angular segments of the different focal lengths are arranged such that the angular segments of the same focal length comprise segments arranged along the two perpendicular axes, thereby enabling to orient the imaging lens structure with respect to a line of sight such that vertically and horizontally oriented segments within the lens region are those having the focal length corresponding to the near field vision, and the angular segments of other orientations with respect to the line of sight are those corresponding to the far field vision.

27. The imaging lens unit of claim 24, wherein the at least two phase coding patterns associated with the lens regions of the at least two different focal lengths respectively are configured to provide extended depth of focus for imaging via said angular segments.

28. The imaging lens of claim 24, wherein the phase coder has one of the following configuration: (i) is a separate phase mask located close to or attached to the lens region along the optical axis; (ii) is a phase mask integral with the lens region.

* * * * *